United States Patent
Van Schalkwyk et al.

(10) Patent No.: US 11,433,210 B2
(45) Date of Patent: Sep. 6, 2022

(54) GASES MIXING AND MEASURING FOR A MEDICAL DEVICE

(71) Applicant: Fisher & Paykel Healthcare Limited, Auckland (NZ)

(72) Inventors: Andre Van Schalkwyk, Auckland (NZ); Anthony James Newland, Auckland (NZ); Rachael Glaves, Auckland (NZ); Wenjie Robin Liang, Auckland (NZ); Winnie Yong Jiang-Foo, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 241 days.

(21) Appl. No.: 15/313,836

(22) PCT Filed: May 27, 2015

(86) PCT No.: PCT/NZ2015/050068
§ 371 (c)(1),
(2) Date: Nov. 23, 2016

(87) PCT Pub. No.: WO2015/183107
PCT Pub. Date: Dec. 3, 2015

(65) Prior Publication Data
US 2017/0197056 A1    Jul. 13, 2017

Related U.S. Application Data

(60) Provisional application No. 62/003,423, filed on May 27, 2014.

(51) Int. Cl.
*A61M 16/10*    (2006.01)
*A61M 16/00*    (2006.01)
(Continued)

(52) U.S. Cl.
CPC .... *A61M 16/1005* (2014.02); *A61M 16/0066* (2013.01); *A61M 16/024* (2017.08);
(Continued)

(58) Field of Classification Search
CPC .............. A61M 16/00; A61M 16/0066; A61M 16/024; A61M 16/10; A61M 16/1005;
(Continued)

(56) References Cited

U.S. PATENT DOCUMENTS

| | | |
|---|---|---|
| 1,269,599 A | 6/1918 | Haber |
| 1,570,781 A | 6/1926 | Ruben |

(Continued)

FOREIGN PATENT DOCUMENTS

| | | |
|---|---|---|
| AU | 2014202639 | 12/2014 |
| CN | 1336536 A | 2/2002 |

(Continued)

OTHER PUBLICATIONS

International Search Report in corresponding International Patent Application No. PCT/NZ2015/050068, dated Oct. 29, 2015, in 7 pages.

(Continued)

*Primary Examiner* — Justine R Yu
*Assistant Examiner* — Matthew D Ziegler
(74) *Attorney, Agent, or Firm* — Knobbe, Martens, Olson & Bear, LLP

(57) ABSTRACT

A gases humidification system includes a measuring chamber and a mixing chamber. The mixing chamber has one or more mixing elements that improve a mixing of gases before reaching the measuring chamber. Ultrasonic sensing is used to measure gases properties or characteristics within the measuring chamber. A baffle or a vane may be used to (Continued)

control and direct the gases flow through the mixing chamber as the gases flow moves into the measuring chamber.

25 Claims, 8 Drawing Sheets

(51) Int. Cl.
*A61M 16/16* (2006.01)
*G01N 29/024* (2006.01)
*A61M 16/12* (2006.01)
*G01F 1/66* (2022.01)
*G01N 29/036* (2006.01)
*G01H 5/00* (2006.01)
*G01F 25/10* (2022.01)
*G01P 5/24* (2006.01)

(52) U.S. Cl.
CPC .......... *A61M 16/12* (2013.01); *A61M 16/122* (2014.02); *A61M 16/16* (2013.01); *G01F 1/66* (2013.01); *G01F 1/662* (2013.01); *G01F 25/10* (2022.01); *G01F 25/15* (2022.01); *G01H 5/00* (2013.01); *G01N 29/024* (2013.01); *G01N 29/036* (2013.01); *G01P 5/245* (2013.01); *A61M 16/161* (2014.02); *A61M 2016/1025* (2013.01); *A61M 2202/0208* (2013.01); *A61M 2205/3334* (2013.01); *A61M 2205/3368* (2013.01); *A61M 2205/3375* (2013.01); *A61M 2205/50* (2013.01); *A61M 2206/14* (2013.01); *A61M 2206/20* (2013.01); *G01N 2291/0212* (2013.01); *G01N 2291/0215* (2013.01); *G01N 2291/02809* (2013.01); *G01N 2291/02836* (2013.01)

(58) Field of Classification Search
CPC .............. A61M 16/1045; A61M 16/12; A61M 16/122; A61M 16/16; A61M 16/161; A61M 16/0003; A61M 16/1075; A61M 16/109; A61M 16/125; A61M 16/127; A61M 16/0051; A61M 16/021; A61M 16/022; A61M 16/026; A61M 2016/102; A61M 2016/1035; A61M 2016/1025; A61M 2016/103; A61M 2202/0208; A61M 2205/33; A61M 2205/3334; A61M 2205/3368; A61M 2205/3375; A61M 2205/50; A61M 2206/14; A61M 2206/20; G01F 1/66; G01F 1/662; G01F 25/0007; G01F 25/0053; G01N 29/024; G01N 29/036; G01N 2291/0212; G01N 2291/0215; G01N 2291/02809; G01N 2291/02836
See application file for complete search history.

(56) References Cited

U.S. PATENT DOCUMENTS

| | | |
|---|---|---|
| 2,283,750 A | 5/1942 | Mikelson |
| 2,568,277 A | 9/1951 | Eltgroth |
| 2,874,564 A | 2/1959 | Martin et al. |
| 2,984,097 A | 5/1961 | Kniazuk et al. |
| 3,120,750 A | 2/1964 | Root, III |
| 3,343,403 A | 9/1967 | Romani et al. |
| 3,468,157 A | 9/1969 | Burk et al. |
| 3,495,628 A | 2/1970 | Boender |
| 3,724,484 A | 4/1973 | Turman |
| 3,762,197 A | 10/1973 | Roof et al. |
| 3,805,590 A | 4/1974 | Ringwall et al. |
| 3,848,457 A | 11/1974 | Behymer |
| 3,863,630 A | 2/1975 | Cavallo |
| 3,926,223 A | 12/1975 | Petzetakis |
| 3,981,176 A | 9/1976 | Jacobs |
| 4,033,808 A | 7/1977 | Petzetakis |
| 4,155,246 A | 5/1979 | Dempster et al. |
| 4,215,409 A | 7/1980 | Strowe |
| 4,220,040 A | 9/1980 | Noguchi et al. |
| 4,255,964 A | 3/1981 | Morison |
| 4,280,183 A | 7/1981 | Santi |
| 4,313,436 A | 2/1982 | Schwanbom et al. |
| 4,326,513 A | 4/1982 | Schulz et al. |
| 4,331,025 A | 5/1982 | Ord, Jr. |
| 4,340,044 A | 7/1982 | Levy et al. |
| 4,345,612 A | 8/1982 | Koni et al. |
| 4,380,167 A | 4/1983 | Longini |
| 4,452,090 A | 6/1984 | Kou et al. |
| 4,520,654 A * | 6/1985 | Terhune ............... G01N 29/024 376/256 |
| 4,531,551 A | 7/1985 | Eichelberger et al. |
| 4,555,932 A | 12/1985 | Crosby, Jr. |
| 4,662,212 A * | 5/1987 | Noguchi ............... G01N 29/024 310/323.21 |
| 4,773,448 A | 9/1988 | Francis |
| 4,889,116 A | 12/1989 | Taube |
| 4,903,736 A | 2/1990 | Baston et al. |
| 4,938,066 A | 7/1990 | Dorr |
| 4,989,595 A | 2/1991 | De Vuono et al. |
| 5,060,506 A | 10/1991 | Douglas |
| 5,060,507 A | 10/1991 | Urmson et al. |
| 5,060,514 A * | 10/1991 | Aylsworth ........... G01N 29/024 73/24.01 |
| 5,127,442 A | 7/1992 | Blomqvist |
| 5,179,862 A | 1/1993 | Lynnworth |
| 5,247,826 A | 9/1993 | Frola et al. |
| 5,285,677 A | 2/1994 | Oehler |
| 5,313,820 A | 5/1994 | Aylsworth |
| 5,343,760 A | 9/1994 | Sultan et al. |
| 5,351,522 A * | 10/1994 | Lura ................... G01N 29/024 73/24.01 |
| 5,359,897 A | 11/1994 | Hamstead et al. |
| 5,365,922 A | 11/1994 | Raemer |
| 5,392,635 A | 2/1995 | Cadet et al. |
| 5,452,621 A | 9/1995 | Aylesworth et al. |
| 5,452,714 A | 9/1995 | Anderson et al. |
| 5,460,175 A | 10/1995 | Foote et al. |
| 5,463,906 A | 11/1995 | Spani et al. |
| 5,490,763 A * | 2/1996 | Abrams ................ F04D 5/00 415/206 |
| 5,503,151 A | 4/1996 | Harnoncourt et al. |
| 5,551,419 A | 9/1996 | Froehlich et al. |
| 5,581,014 A | 12/1996 | Douglas |
| 5,591,292 A | 1/1997 | Blomqvist |
| 5,625,140 A | 4/1997 | Cadet et al. |
| 5,627,323 A | 5/1997 | Stern |
| 5,640,951 A | 6/1997 | Huddart et al. |
| 5,701,883 A | 12/1997 | Hete et al. |
| 5,792,665 A | 8/1998 | Morrow, III |
| 5,809,997 A | 9/1998 | Wolf |
| 5,823,186 A | 10/1998 | Rossen et al. |
| 5,917,135 A | 6/1999 | Michaels et al. |
| 6,039,696 A | 3/2000 | Bell |
| 6,105,649 A | 8/2000 | Levingston et al. |
| 6,123,074 A | 9/2000 | Hete et al. |
| 6,138,674 A | 10/2000 | Gull et al. |
| 6,142,149 A | 11/2000 | Steen |
| 6,178,827 B1 * | 1/2001 | Feller ..................... G01F 1/662 73/861.22 |
| 6,279,379 B1 | 8/2001 | Logue et al. |
| 6,397,841 B1 | 6/2002 | Kenyon et al. |
| 6,487,916 B1 | 12/2002 | Gomm et al. |
| 6,537,405 B1 | 3/2003 | Henderson et al. |
| 6,543,449 B1 | 4/2003 | Woodring et al. |
| 6,581,595 B1 | 6/2003 | Murdock et al. |
| 6,629,934 B2 | 10/2003 | Mault et al. |
| 6,634,356 B1 | 10/2003 | O'Dea et al. |
| 6,910,481 B2 | 6/2005 | Kimmel et al. |
| 7,063,668 B2 | 6/2006 | Cardelius et al. |
| 7,066,175 B2 | 6/2006 | Hamilton et al. |
| 7,111,624 B2 | 9/2006 | Thudor et al. |
| 7,183,552 B2 | 2/2007 | Russell |

(56) References Cited

U.S. PATENT DOCUMENTS

| | | | |
|---|---|---|---|
| 7,370,651 B2 | 5/2008 | Holder | |
| 7,432,508 B2 | 10/2008 | Daniels et al. | |
| 7,448,376 B2 | 11/2008 | Lepel | |
| 7,501,630 B2 | 3/2009 | Russell | |
| 7,509,957 B2 | 3/2009 | Duquette et al. | |
| 7,606,668 B2 | 10/2009 | Pierry et al. | |
| 7,810,497 B2 | 10/2010 | Pittman et al. | |
| 8,042,535 B2 | 10/2011 | Kenyon et al. | |
| 8,047,082 B2 | 11/2011 | Bierl | |
| 8,100,124 B2 | 1/2012 | Becker et al. | |
| 8,381,722 B2 | 2/2013 | Berthon-Jones | |
| 8,485,183 B2 * | 7/2013 | Masic | G01F 1/00 128/204.21 |
| 8,561,611 B2 | 10/2013 | Shissler et al. | |
| 8,616,202 B2 * | 12/2013 | Tatkov | A61M 16/1095 128/203.17 |
| 8,746,037 B2 | 6/2014 | Matsuzaki | |
| 8,752,544 B2 | 6/2014 | Bottom | |
| 8,875,587 B2 | 11/2014 | Wiest et al. | |
| 9,119,933 B2 | 9/2015 | Bedford et al. | |
| 9,149,590 B2 | 10/2015 | Wallen | |
| 9,302,066 B2 | 4/2016 | Bertinetti et al. | |
| 9,649,459 B2 | 5/2017 | Taylor et al. | |
| 10,357,629 B2 | 7/2019 | Barker et al. | |
| 2002/0062681 A1 | 5/2002 | Livingston | |
| 2003/0065274 A1 | 4/2003 | Mault et al. | |
| 2004/0211244 A1 | 10/2004 | Cardelius et al. | |
| 2005/0121033 A1 | 6/2005 | Starr et al. | |
| 2005/0125170 A1 * | 6/2005 | Gysling | G01F 1/666 702/48 |
| 2005/0223795 A1 * | 10/2005 | Gerder | A61B 5/087 73/204.21 |
| 2006/0042638 A1 | 3/2006 | Niklewski et al. | |
| 2006/0113690 A1 | 6/2006 | Huddart et al. | |
| 2006/0156828 A1 * | 7/2006 | Konzelmann | G01F 5/00 73/861.25 |
| 2006/0158956 A1 * | 7/2006 | Laugharn | B01F 11/02 366/127 |
| 2006/0283450 A1 | 12/2006 | Shissler et al. | |
| 2007/0044799 A1 | 3/2007 | Hete et al. | |
| 2007/0062531 A1 | 3/2007 | Fisher et al. | |
| 2007/0125374 A1 | 6/2007 | Smith et al. | |
| 2007/0245802 A1 * | 10/2007 | Austerlitz | G01N 29/024 73/24.01 |
| 2007/0283958 A1 | 12/2007 | Naghavi | |
| 2008/0041381 A1 | 2/2008 | Tham et al. | |
| 2008/0060647 A1 | 3/2008 | Messenger et al. | |
| 2008/0092891 A1 | 4/2008 | Cewers | |
| 2008/0156328 A1 | 7/2008 | Taube | |
| 2009/0020120 A1 | 1/2009 | Schatzl et al. | |
| 2009/0056715 A1 | 3/2009 | Cortez, Jr. et al. | |
| 2009/0107501 A1 | 4/2009 | Krieger | |
| 2009/0145428 A1 | 6/2009 | Sward et al. | |
| 2009/0178490 A1 * | 7/2009 | Konzelmann | G01F 1/662 73/861.29 |
| 2009/0241953 A1 | 10/2009 | Vandine et al. | |
| 2010/0006098 A1 | 1/2010 | McGinnis et al. | |
| 2010/0126249 A1 | 5/2010 | Matsuzaki | |
| 2010/0218591 A1 | 9/2010 | Rhodes et al. | |
| 2010/0224191 A1 | 9/2010 | Dixon et al. | |
| 2011/0120462 A1 | 5/2011 | Tatkov | |
| 2011/0209558 A1 * | 9/2011 | Sugiura | G01F 1/662 73/861.18 |
| 2011/0314897 A1 | 12/2011 | Schellekens et al. | |
| 2012/0006326 A1 | 1/2012 | Ahmad | |
| 2012/0055340 A1 | 3/2012 | Wilkinson et al. | |
| 2012/0065533 A1 | 3/2012 | Carillo, Jr. et al. | |
| 2012/0109536 A1 * | 5/2012 | Pasveer | G01N 29/024 702/24 |
| 2012/0125121 A1 | 5/2012 | Gottlieb et al. | |
| 2012/0271188 A1 * | 10/2012 | Van Kesteren | A61B 5/0095 600/532 |
| 2013/0008438 A1 * | 1/2013 | Sugawara | A61M 16/10 128/202.24 |
| 2013/0239960 A1 | 9/2013 | Bertinetti et al. | |
| 2013/0263854 A1 | 10/2013 | Taylor et al. | |
| 2013/0267863 A1 | 10/2013 | Orr | |
| 2014/0007878 A1 | 1/2014 | Armitstead et al. | |
| 2014/0034051 A1 | 2/2014 | Addington et al. | |
| 2014/0137859 A1 | 5/2014 | Wilkinson et al. | |
| 2014/0261414 A1 | 9/2014 | Weitzel et al. | |
| 2014/0311253 A1 * | 10/2014 | Iwasa | G01F 1/662 73/861.21 |
| 2015/0048530 A1 * | 2/2015 | Cheung | A61M 16/16 261/129 |
| 2015/0059745 A1 | 3/2015 | Barker et al. | |
| 2015/0107587 A1 | 4/2015 | Zhang | |
| 2015/0136129 A1 | 5/2015 | Mahadevan et al. | |
| 2015/0283339 A1 | 10/2015 | Mahadevan et al. | |
| 2016/0082220 A1 | 3/2016 | Barker et al. | |
| 2016/0114121 A1 | 4/2016 | Holley et al. | |
| 2016/0151601 A1 | 6/2016 | Cardelius et al. | |
| 2016/0228670 A1 | 8/2016 | Av-Gay et al. | |
| 2016/0287824 A1 | 10/2016 | Chang | |
| 2016/0354573 A1 | 12/2016 | Buswell et al. | |
| 2018/0236191 A1 | 8/2018 | Martin et al. | |
| 2019/0269874 A1 | 9/2019 | Barker et al. | |

FOREIGN PATENT DOCUMENTS

| | | |
|---|---|---|
| CN | 1455865 | 11/2003 |
| CN | 1817378 A | 8/2006 |
| CN | 101152592 | 4/2008 |
| CN | 101318049 A | 12/2008 |
| CN | 101554510 A | 10/2009 |
| CN | 201379872 Y | 1/2010 |
| CN | 101680859 A | 3/2010 |
| CN | 101861182 | 10/2010 |
| CN | 102105189 A | 6/2011 |
| CN | 102261937 A | 11/2011 |
| CN | 101252966 B | 7/2012 |
| CN | 102316920 B | 9/2015 |
| DE | 404809 | 10/1924 |
| EP | 0896671 B1 | 4/1997 |
| EP | 0788805 A2 | 8/1997 |
| EP | 813060 | 12/1997 |
| EP | 1083427 B1 | 3/2001 |
| EP | 1138341 | 10/2001 |
| EP | 1205747 A2 | 5/2002 |
| EP | 1286159 A1 | 2/2003 |
| EP | 1961439 | 8/2008 |
| EP | 2154526 A1 | 2/2010 |
| EP | 2200687 B1 | 6/2015 |
| EP | 2833953 B1 | 1/2019 |
| GB | 191408838 A | 10/1914 |
| GB | 2087559 | 5/1982 |
| JP | 55-004528 | 1/1980 |
| JP | S58-190439 | 12/1983 |
| JP | H01-321508 | 12/1989 |
| JP | 10-073574 | 3/1998 |
| JP | 2001-120661 | 5/2001 |
| JP | 2011-120661 | 5/2001 |
| JP | 2002-214012 | 7/2002 |
| JP | 2002-306603 | 10/2002 |
| JP | 2002-306603 A | 10/2002 |
| JP | 2005-537083 | 12/2005 |
| JP | 2008-518640 | 6/2008 |
| JP | 2010-537779 | 12/2010 |
| JP | 2011-521705 | 7/2011 |
| JP | 2018-118085 A | 8/2018 |
| WO | WO 95/28193 | 10/1995 |
| WO | WO 2000/045883 | 8/2000 |
| WO | WO 03/090903 | 11/2003 |
| WO | WO 2004/039444 | 5/2004 |
| WO | WO 2004/069922 | 8/2004 |
| WO | WO 2004/112873 | 12/2004 |
| WO | WO 2007/004898 | 1/2007 |
| WO | WO 2007/069922 | 6/2007 |
| WO | WO 2007/103855 A2 | 9/2007 |
| WO | WO 2008/149868 | 5/2008 |
| WO | WO 2009/045198 | 4/2009 |
| WO | WO 2009/052631 | 4/2009 |
| WO | WO 2009/058081 | 5/2009 |

(56) References Cited

FOREIGN PATENT DOCUMENTS

| WO | WO 2009/145646 A1 | 12/2009 |
|---|---|---|
| WO | WO 2010/084183 A2 | 7/2010 |
| WO | WO 2011/010191 | 1/2011 |
| WO | WO 2011/058196 A1 | 5/2011 |
| WO | WO 2011/0157196 | 5/2011 |
| WO | WO 2011/075030 | 6/2011 |
| WO | WO 2012/021557 | 2/2012 |
| WO | WO 2013/128365 | 9/2013 |
| WO | WO 2013/137753 | 9/2013 |
| WO | WO 2013/151447 | 10/2013 |
| WO | WO 2014/059405 | 4/2014 |
| WO | WO 2015/038013 | 3/2015 |
| WO | WO 2015/183107 | 12/2015 |
| WO | WO 2015/183107 A1 | 12/2015 |
| WO | WO 2017/095241 | 6/2017 |

OTHER PUBLICATIONS

International Preliminary Report on Patentability in corresponding International Patent Application No. PCT/NZ2015/050068, dated Dec. 8, 2016, in 9 pages.

Markus Joos et al., "An ultrasonic sensor for the analysis of binary gas mixtures", Sensors and Actuators B: Chemical, vol. 16, Issues 1-3, Oct. 1993, pp. 413-419.

H. Toda et al., "High-speed gas concentration measurement using ultrasound", Sensors and Actuators A: Physical, vol. 144, Issue 1, May 28, 2008, pp. 1-6.

J.C. Vyas et al., "A non-invasive ultrasonic gas sensor for binary gas mixtures", Sensors and Actuators B: Chemical, vol. 115, Issue 1, May 23, 2006, pp. 28-32.

Office Action in corresponding Chinese Patent Application No. 201711259795.8, dated Feb. 3, 2020, in 9 pages.

Li Daohua, "Sensor Circuit Analysis and Design," Wuhan University Press, Mar. 2000, pp. 203-209.

* cited by examiner

GASES MIXING AND MEASURING FOR A MEDICAL DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to a medical gases delivery system. More particularly, certain features, aspects, and advantages of the present disclosure relate to a respiratory gases delivery system that mixes different respiratory gases and measures properties or characteristics of the mixed gases.

Description of Related Art

A gases delivery system may be used to provide respiratory gases to a patient. The gases delivery system may include a humidification device to condition the gases provided to the patient. The gases may be heated and/or humidified prior to delivery. Gases are delivered to the patient via a tube that is in fluid communication with a patient interface. Gases delivered to patients at 100% relative humidity and 37° C. generally mimic properties of air resulting from the transformation that occurs as air passes through airways from the nose to the lungs. This can promote efficient gases exchange and ventilation in the lungs, aid defense mechanisms in the airways, and increase patient comfort during treatment. In some cases, a gases delivery system used for oxygen therapy may provide oxygen to the patient. The oxygen may be mixed with air to provide a desired or targeted therapy to the patient. In such cases, a gases delivery system may monitor the concentration of oxygen to ensure that the desired or targeted amount is being delivered to the patient and to reduce or prevent wastage of oxygen.

SUMMARY

An aspect of at least one of the embodiments disclosed herein includes the realization that there are problems associated with typical approaches to mixing gases and measuring properties of mixed gases. Typical gases delivery systems may use a combination of gases, such as oxygen and air, but may not mix these sufficiently. Sensors used to measure properties of such a combination of gases may produce unreliable results. Flow rate and gases concentration measurements may both be affected by insufficient gases mixing. A mixing chamber may be used to enable sufficient mixing of gases; however, the size of a typical mixing chamber may cause the gases delivery system to be bulky or undesirably large. Typical mixing chambers may induce turbulence to encourage mixing between gases; however, turbulence may result in an acoustically noisy process and may lead to difficulties when measuring gases properties such as gases flow rate, gases concentration, or the like. Some systems may use ultrasonic sensors to measure a gases property such as concentration by inducing pressure waves that are generally perpendicular to the flow direction of the gases. Some of these systems may position a pair of ultrasonic sensors in close proximity to each other, which may increase the sensitivity of the system. In such systems, one or more additional sensors may be used to determine the gases flow rate.

The gases delivery systems and methods disclosed herein constitute improvements over typical gases delivery systems. A measurement apparatus of a gases delivery system can comprise a measuring chamber positioned within a mixing chamber in a coaxial arrangement. The coaxial chamber arrangement may increase a gases path length through the measurement apparatus while remaining more compact relative to linear or serial chamber arrangements. The mixing chamber can be configured to sufficiently mix gases before the gases move to the measuring chamber. A mixing element within the mixing chamber may induce swirling of the gases to promote mixing, this being accomplished with little or no turbulence. At least one ultrasonic sensor can be located at each end of the measuring chamber to measure gases properties or characteristics along the gases flow. Gases concentration, flow rate, and velocity can be measured using the ultrasonic sensors.

Other embodiments can comprise a mixing chamber comprising a baffle configured to promote turbulent mixing of the gases and a vane configured to linearize the gases to improve measurement of the gases properties in the measuring chamber.

At least one aspect of the present disclosure relates to a gases measurement apparatus comprising a gases measuring chamber, a controller, and first and second ultrasonic sensors. The gases measuring chamber comprises a gases flow path from a first end to a second end of the gases measuring chamber. A downstream direction is defined along the gases flow path from the first end to the second end. An upstream direction is defined along the gases flow path from the second end to the first end. The first ultrasonic sensor is positioned at the first end of the gases measuring chamber. The first ultrasonic sensor is configured to transmit a downstream acoustic pulse train in a first measurement phase. The first ultrasonic sensor is configured to detect an upstream acoustic pulse train in a second measurement phase. The first ultrasonic sensor is configured to send a signal to the controller. The second ultrasonic sensor is positioned at the second end of the gases measuring chamber. The second ultrasonic sensor is configured to transmit the upstream acoustic pulse train in the second measurement phase. The second ultrasonic sensor is configured to detect the downstream acoustic pulse train in the first measurement phase. The second ultrasonic sensor is configured to send a signal to the controller. The controller is configured to determine a characteristic of the gases based at least in part on a signal received from the first ultrasonic sensor and a signal received from the second ultrasonic sensor.

The gases can comprise two gases. The two gases can comprise oxygen and air. The downstream acoustic pulse train can comprise a plurality of acoustic pulses. The upstream acoustic pulse train can comprise a plurality of acoustic pulses. The downstream acoustic pulse train can comprise a single acoustic pulse. The upstream acoustic pulse train can comprise a single acoustic pulse. The characteristic of the gases can comprise at least one of gases concentration, flow rate, or velocity. The first ultrasonic sensor can be configured to be excited at a natural resonant frequency. The second ultrasonic sensor can be configured to be excited at a natural resonant frequency. The controller can be configured to determine a downstream time of flight for the downstream acoustic pulse train. The controller can be configured to determine an upstream time of flight for the upstream acoustic pulse train. The controller can be configured to determine the characteristic of the gases based at least in part on the downstream time of flight and the upstream time of flight.

At least one aspect of the present disclosure relates to a method for determining a characteristic of gases flowing through an apparatus along a gases flow path from a first end to a second end of the apparatus, the apparatus comprising a first ultrasonic sensor positioned at the first end and a second ultrasonic sensor positioned at the second end. A downstream direction is defined along the gases flow path from the first end to the second end. An upstream direction is defined along the gases flow path from the second end to the first end.

The method comprises transmitting a downstream acoustic pulse train from the first ultrasonic sensor. The method comprises detecting the downstream acoustic pulse train at the second ultrasonic sensor. The method comprises determining a downstream time of flight based at least in part on the downstream acoustic pulse train. The method comprises transmitting an upstream acoustic pulse train from the second ultrasonic sensor. The method comprises detecting the upstream acoustic pulse train at the first ultrasonic sensor. The method comprises determining an upstream time of flight based at least in part on the upstream acoustic pulse train. The method comprises determining the characteristic of the gases based at least in part on the downstream time of flight and the upstream time of flight. The downstream acoustic pulse train can comprise a plurality of acoustic pulses. The upstream acoustic pulse train can comprise a plurality of acoustic pulses. The downstream acoustic pulse train can comprise a single acoustic pulse. The upstream acoustic pulse train can comprise a single acoustic pulse.

The method can comprise transmitting a second downstream acoustic pulse train from the first ultrasonic sensor. The method can comprise detecting the second downstream acoustic pulse train at the second ultrasonic sensor. The method can comprise determining the downstream time of flight based at least in part on an average of the downstream acoustic pulse train and the second downstream acoustic pulse train. The method can comprise transmitting a second upstream acoustic pulse train from the second ultrasonic sensor. The method can comprise detecting the second upstream acoustic pulse train at the first ultrasonic sensor. The method can comprise determining the upstream time of flight based at least in part on an average of the upstream acoustic pulse train and the second upstream acoustic pulse train. The characteristic of the gases can comprise at least one of gases concentration, flow rate, or velocity. Transmitting a downstream acoustic pulse train from the first ultrasonic sensor can comprise exciting the first ultrasonic sensor at a natural resonant frequency. Transmitting an upstream acoustic pulse train from the second ultrasonic sensor can comprise exciting the second ultrasonic sensor at the natural resonant frequency.

The gases can comprise oxygen and air. Determining the characteristic of the gases can comprise determining an oxygen concentration as a volume percentage by multiplying the concentration in air of gases other than oxygen with the difference between an average downstream and upstream time of flight for the gases and an average downstream and upstream time of flight for air, dividing that by the difference between an average downstream and upstream time of flight for oxygen and an average downstream and upstream time of flight for air, and then adding to the result the oxygen concentration of air.

Determining the characteristic of the gases can comprise determining a flow rate in liters per minute for a given oxygen concentration by subtracting the downstream time of flight from the upstream time of flight, subtracting from that a calibrated correction for the gases mixture, and then multiplying the result by a constant factor for geometric aspects of the apparatus. The calibrated correction for the gases mixture can be determined by subtracting a calibrated correction for air from a calibrated correction for oxygen, multiplying the result by the difference between the given oxygen concentration and 20.9 (the oxygen concentration of air expressed as a percentage), dividing that result by the concentration as a volume percentage of gases in air other than oxygen, and then adding the calibrated correction for air.

At least one aspect of the present disclosure relates to a gases delivery apparatus comprising a gases mixing chamber and a gases measuring chamber. The gases mixing chamber is configured to receive gases from a gases source. The gases mixing chamber comprises a gases flow path from a first end to a second end of the gases mixing chamber. The gases mixing chamber comprises at least one mixing element situated within the gases flow path. The gases measuring chamber is configured to receive gases from the gases mixing chamber. The gases measuring chamber comprises a gases flow path from a first end to a second end of the gases measuring chamber. The gases measuring chamber is situated coaxially within the gases mixing chamber. The at least one mixing element is configured to mix gases in the gases flow path of the gases mixing chamber before the gases enter the gases flow path of the gases measuring chamber.

The at least one mixing element can comprise a vane that is configured to reduce turbulence in gases that flow from the gases flow path of the gases mixing chamber to the gases flow path of the gases measuring chamber. The at least one mixing element can comprise a baffle that is configured to increase the length of the gases flow path of the gases mixing chamber. The gases mixing chamber can be configured to receive two or more gases. The gases mixing chamber can be configured to mix the received gases. The apparatus can comprise a first ultrasonic sensor positioned at the first end of the gases measuring chamber. The apparatus can comprise a second ultrasonic sensor positioned at the second end of the gases measuring chamber.

BRIEF DESCRIPTION OF THE DRAWINGS

These and other features, aspects, and advantages of the disclosed systems and methods will be described with respect to the following figures, which are intended to illustrate and not to limit the disclosed embodiments.

DETAILED DESCRIPTION

A gases delivery system can be configured to deliver respiratory gases to a patient. The respiratory gases can be conditioned to have targeted or desirable properties. These properties can be selected to provide therapeutic effects for a patient, to increase comfort of a patient during therapy, or to otherwise improve respiration for the patient. Some gases delivery systems can be configured to provide a mixture of gases to a patient. For example, a gases delivery system can be configured to provide air mixed with oxygen to a patient. The concentration of oxygen in the gases mixture can be measured and maintained by the gases delivery system using a control feedback loop. For example, the gases delivery system can comprise a measurement apparatus configured to measure the concentrations of component gases in the gases mixture and a controller configured to control a valve to regulate the contribution of at least one of the component gases to the gases mixture, based at least in part on the measurements provided by the measurement apparatus. The measurement apparatus can comprise a mixing chamber configured to efficiently mix the component gases prior to entry of the mixed gases into a measuring chamber where the mixed gases can be measured. The accuracy of measurements provided by such a measurement apparatus may be superior to measurements provided by other devices that do not sufficiently mix the gases prior to measurement.

As an example, a gases delivery system can be configured to mix two component gases and control the contribution of at least one of the component gases to the gases mixture via one or more control valves. The gases delivery system can be configured to mix the component gases into a substantially homogeneous binary mixture. The gases delivery system can comprise ultrasonic transducers or sensors configured to generate and detect pressure waves along the flow of gases through a measuring chamber to determine gas concentrations or relative ratios of the component gases. The output of the ultrasonic sensors can be signals indicative of properties or characteristics of the gases. The gases delivery system can comprise a mixing chamber configured to direct the flow of gases along a spiralling gases flow path around the outside of the measuring chamber, the measuring chamber being situated coaxially within the mixing chamber. A coaxial chamber arrangement can provide a relatively long gases flow path to promote efficient mixing of gases as well as a relatively long distance between the ultrasonic sensors to improve measurement accuracy. In some embodiments, the gases delivery system can comprise baffles and/or vanes. The gases delivery system can operate the one or more control valves based at least in part on measurements of concentrations of component gases to maintain a targeted or desired relative ratio of gases in the gases mixture.

Gases Delivery System

Figure 1:
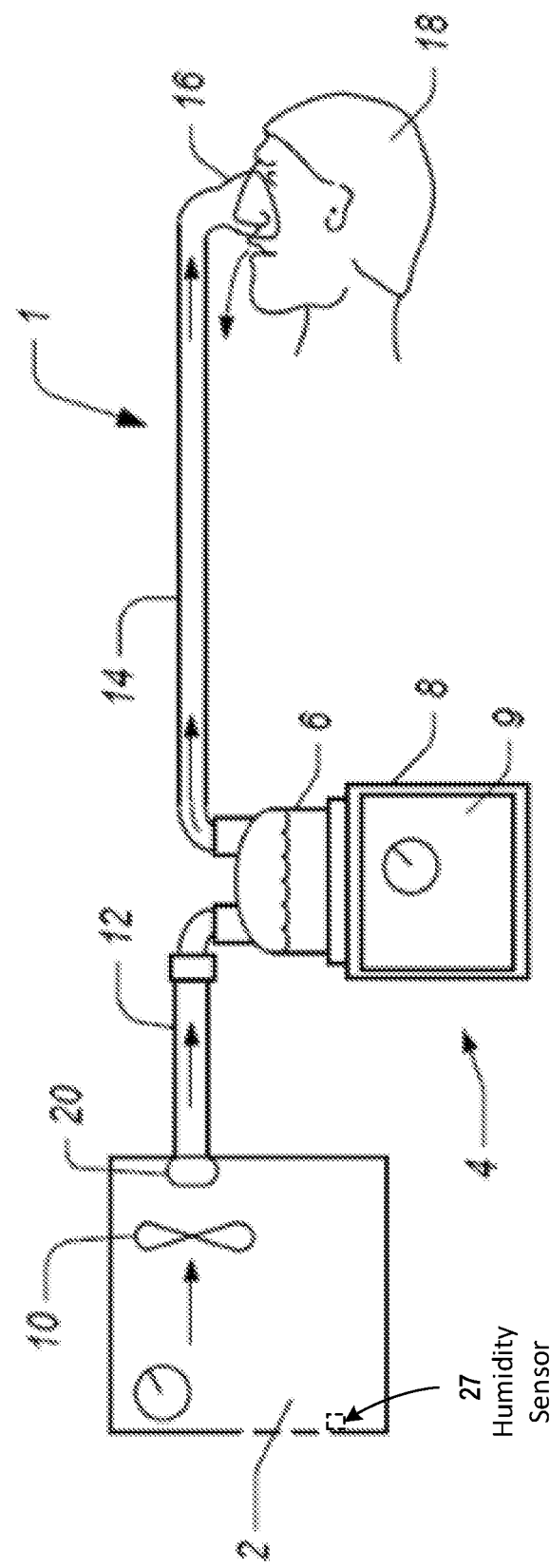
FIG. 1 illustrates an example embodiment of a gases delivery system.

FIG. 1 illustrates an example gases delivery system 1 configured to deliver respiratory gases to a patient 18. The gases delivery system 1 comprises a blower assembly 2, a humidifier 4, a blower conduit 12, a patient conduit 14, and a patient interface 16. The blower assembly 2 comprises a blower 10 and a measurement apparatus 20. The humidifier 4 comprises a humidification chamber 6 and a heating device 8 configured to heat fluids within the humidification chamber 6. In some embodiments, the blower conduit 12 transports gases from the blower assembly 2 to the humidifier 4 and the patient conduit 14 transports humidified gases from the humidifier 4 to the patient interface 16. In some embodiments, each of the blower conduit 12 and the patient conduit 14 may comprise an inspiratory conduit, an expiratory conduit, a dry line, or any other form of conduit, tube, or circuit configured to connect the patient 18 to a gases source. The patient 18 receives the humidified gases via the patient interface 16.

The blower 10 as herein described can comprise a gases source, a ventilation device, a flow generator, a fan, or a combination of these or the like. In some embodiments, the blower 10 is configured to provide air to the measurement apparatus 20. In some embodiments, the measurement apparatus 20 is further configured to receive a second gas or additional gases to mix with the air provided by the blower 10.

The patient interface 16 as herein described can comprise a nasal mask, an oral mask, a full face mask, a nasal cannula, nasal pillows, a tracheal mask, insufflation device, or the like. The systems and methods disclosed herein may be used with invasive or non-invasive therapies, and, in some embodiments, with laparascopic therapies.

The gases delivered to the patient 18 can comprise air, oxygen, carbon dioxide, nitrous oxide, or a combination of any of the gases listed above. It is to be understood that other gases or combinations of gases may also fall within the scope of the present disclosure. As an example, the measurement apparatus 20 can be configured to mix two component gases to provide a binary gases mixture to the patient 18. Each of the component gases in a binary gases mixture may comprise a pure gas or a mixture of gases. A particular example of a binary gases mixture is a mixture of oxygen and air, where air and oxygen are considered component gases of the binary gases mixture even though air is itself a mixture of gases that includes oxygen. The present disclosure will describe apparatus and systems operating on a binary gases mixture of oxygen and air, but it is to be understood that the apparatus and systems will operate in similar fashion on any binary gases mixture.

The measurement apparatus 20 can be configured to mix gases from the blower 10 and/or an additional source of gases to provide a substantially well-mixed gases mixture to the patient 18. As used herein, a substantially well-mixed gases mixture can comprise a substantially homogeneous gases mixture. As an example, a substantially homogeneous gases mixture can refer to a gases mixture that is substantially mixed and that has a generally uniform temperature (e.g., a temperature that is sufficiently consistent or uniform such that variations within the mixture are not clinically relevant). As another example, a substantially homogeneous gases mixture can refer to a gases mixture that is substantially uniform with respect to a gases concentration gradient and/or a temperature gradient, such that any differences between high and low measurements of concentration and/or temperature are not clinically relevant. In contrast, a non-homogeneous gases mixture, for example, may display transient changes in gases properties or characteristics (e.g., flow rate or temperature) that may lead to inaccuracies in gases measurements. It may be advantageous for the measurement apparatus 20 to provide a substantially homogeneous gases mixture because more accurate gases measurements may be achieved more quickly for a substantially homogeneous gases mixture than for a non-homogeneous gases mixture.

In the gases delivery system 1, a transient state (e.g., a period of time during which a concentration of gases is changing) may be shorter than for a system without the measurement apparatus 20, which may allow for faster sampling rates. Thus, the time it takes to detect changes in the concentration of gases can be similar to the time it takes for the gases to transit through the measurement apparatus 20. The time taken for these changes to be detected by the measurement apparatus 20 may depend, at least in part, on the volume of the measurement apparatus 20 and the flow rate of gases through the gases delivery system 1.

Accuracy of sensing may be improved due at least in part to features of the measurement apparatus 20 that increase heat transfer from the gases flowing through the measurement apparatus 20 to a housing of the measurement apparatus 20 and reduce heat transfer from the gases to the environment, such as but not limited to tracks formed on a surface of a printed circuit board (PCB) or a moulded component, a conductive path assembled into the measurement apparatus 20, or the like. This may help to reduce the influence of stem effects on measurement accuracy. High flow rates near a wall of the housing may lead to a high rate of heat transfer between the gases and the housing, which may improve the response time of the materials of the housing to temperature changes and thus ensure that the housing temperature remains generally uniform during a measurement phase. This may be important when determining gases concentration based at least in part on the influence of temperature on the relationship of the actual distance between the sensors and a calibrated distance, which may in turn affect the accuracy of the calculated oxygen concentration. Material properties of the housing can be chosen to reduce or minimize dimensional changes that occur with changes in temperature, which may affect the measurement path length, thereby reducing sensitivity to external parameters.

Oxygen, or other supplementary gases such as but not limited to carbon dioxide, may be supplied to the gases delivery system 1 from a wall source, a gases bottle, or the like. In some embodiments, the supplementary gases can be supplied to the gases delivery system 1 through the measurement apparatus 20.

The gases delivery system 1 can comprise a control system 9 configured to receive measurements or signals from sensors in the gases delivery system 1, control delivery of power to the heating device 8, receive signals from the measurement apparatus 20, control speed or flow rate of the blower 10, and the like. The control system 9 can comprise a controller and data storage device. The controller can comprise one or more microprocessors, application-specific integrated circuits (ASICs), field programmable gate arrays, or the like. The controller can be configured to execute computer executable instructions stored on the data storage device. The data storage device can comprise one or more non-transitory storage devices such as solid state drives, hard disk drives, ROMs, EEPROMs, RAM, and the like. In some embodiments, the control system 9 can be a part of the humidifier 4, part of the blower assembly 2, or part of both the humidifier 4 and the blower assembly 2.

Measurement Apparatus

Figure 2:
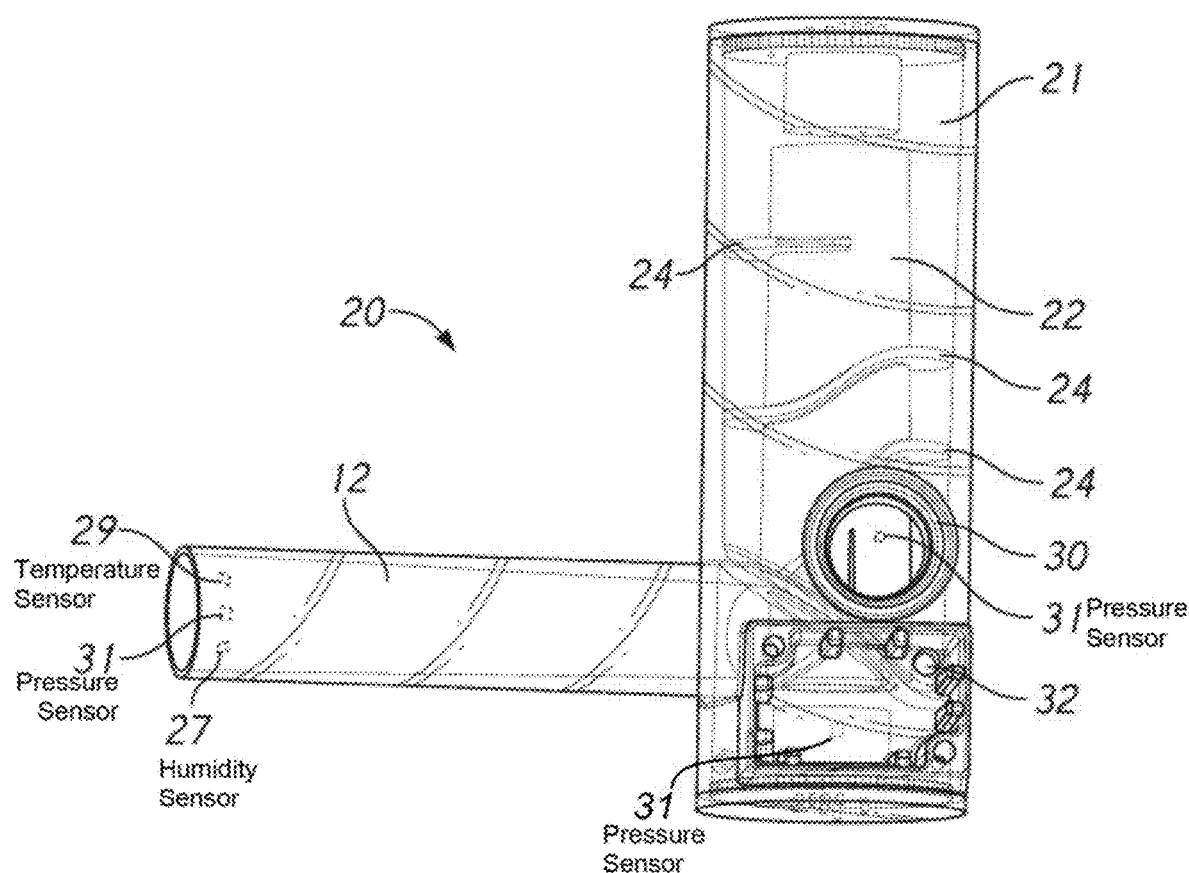
FIGS. 2-4 illustrate an example embodiment of a mixing chamber and a measuring chamber in a coaxial chamber arrangement.

FIG. 2 illustrates an example embodiment of the measurement apparatus 20 configured in a coaxial arrangement. The measurement apparatus 20 comprises a mixing chamber 21 that is an outer chamber of the coaxial arrangement. The coaxial arrangement provides a compact design for the measurement apparatus 20 while allowing for an extended gases flow path which helps to ensure a substantially well-mixed gases mixture. Thus, the measurement apparatus 20 may be more compact than a measurement apparatus with a non-coaxial arrangement. The mixing chamber 21 comprises a mixing element 24. The mixing element 24 may extend the length of the gases flow path through the mixing chamber 21.

Air enters the mixing chamber 21, such as from the blower 10, via an air inlet 30. Oxygen, or another supplementary gas or combination of gases, enters the mixing chamber 21 via an oxygen inlet 32. The inner diameter of the oxygen inlet 32 can be substantially smaller than that of the air inlet 30. One advantage of such a configuration is that the oxygen will enter the mixing chamber 21 at a higher velocity than will the air. This can encourage the air to travel along a longer path length, and may also increase the time that the air and the oxygen are in contact with each other, promoting increased mixing of the air and the oxygen. The air inlet 30 may be positioned such that it is offset from the oxygen inlet 32. The oxygen inlet 32 may be located such that the oxygen does not pass near the air inlet 30 where it could be redirected towards the blower 10, as that may result in a loss of oxygen.

Figure 3:
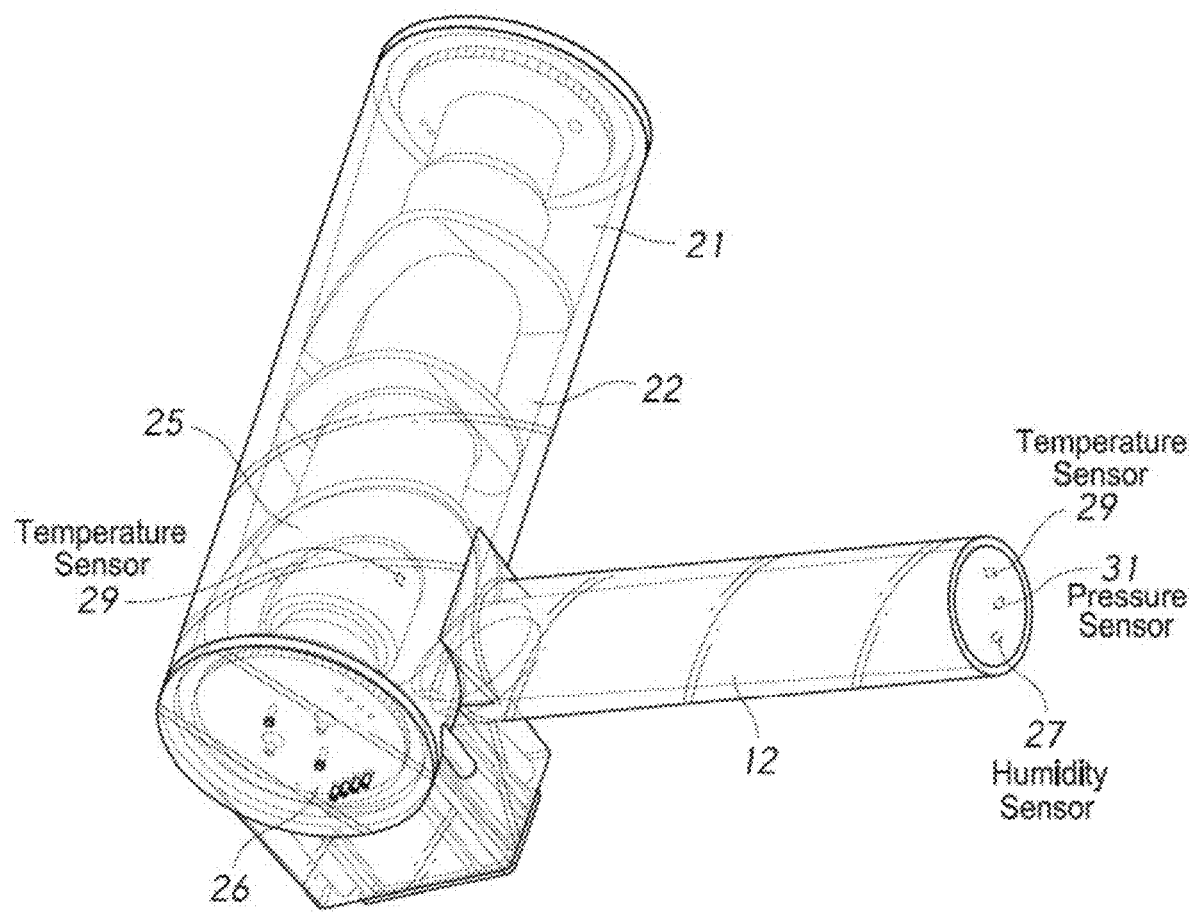
Figure 4:
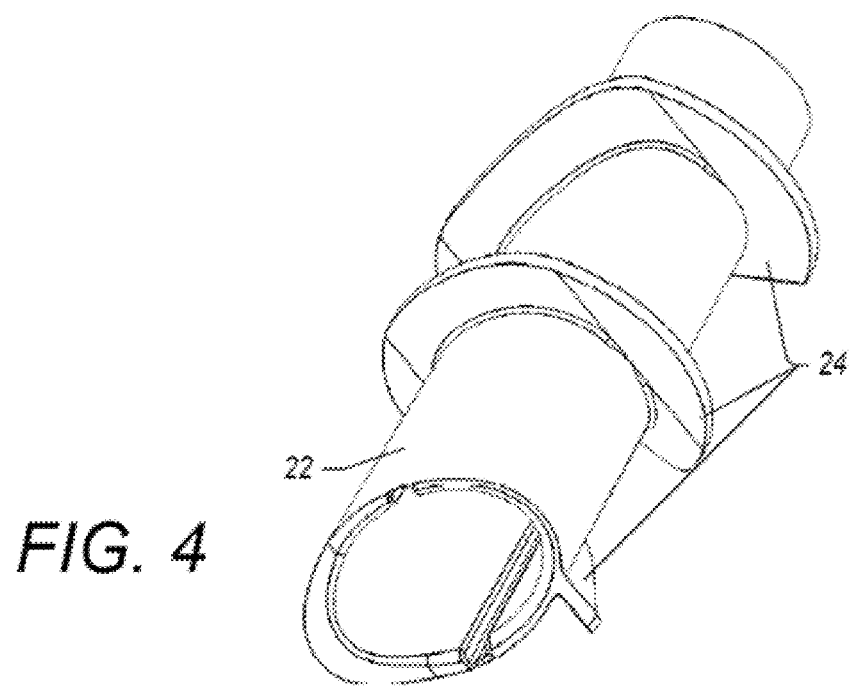

The mixing element 24 is located in the mixing chamber 21 of the measurement apparatus 20. The mixing element 24 promotes a swirling flow of the air and the oxygen around the mixing chamber 21 and towards the measuring chamber 22. FIG. 4 illustrates the mixing element 24 apart from the mixing chamber 21. A swirling flow promotes gases mixing, which may be important with respect to determining gases properties and for generating predictable measurements, particularly at different flow rates. The swirling flow can also maintain a generally symmetric and stable gases profile, and can reduce or eliminate a varying axial component of the gases flow. The swirling flow may also contribute to an acoustically quieter system. FIG. 3 illustrates a wall 25 that separates the gases in the mixing chamber 21 from the mixed gases in the measuring chamber 22.

In some embodiments, the measuring chamber 22 is conical in shape. For example, an entrance of the measuring chamber 22 can be larger than an exit of the measuring chamber 22. An inner diameter of the measuring chamber 22 can decrease along the direction of flow. In certain implementations, an inner wall of the measuring chamber 22 can form an angle with a longitudinal axis of the measuring chamber 22 of less than or equal to about 5 degrees, less than or equal to about 4 degrees, less than or equal to about 3 degrees, or less than or equal to about 1.5 degrees. In some implementations, an entrance of the measuring chamber 22 can be larger than an exit of the measuring chamber 22 by about 5%, by about 3%, or by about 2%. For example, where an inner wall of the measuring chamber 22 is substantially conical, gases can enter the measuring chamber 22 through an entrance that has a radius that is at least about 2-3% larger than a radius of an exit through which gases leave the measuring chamber 22. In some embodiments, a cross-sectional width of the measuring chamber 22 decreases along the direction of flow of gases. The decrease in cross-sectional width is not necessarily linear, but can have any suitable form.

Figure 5:
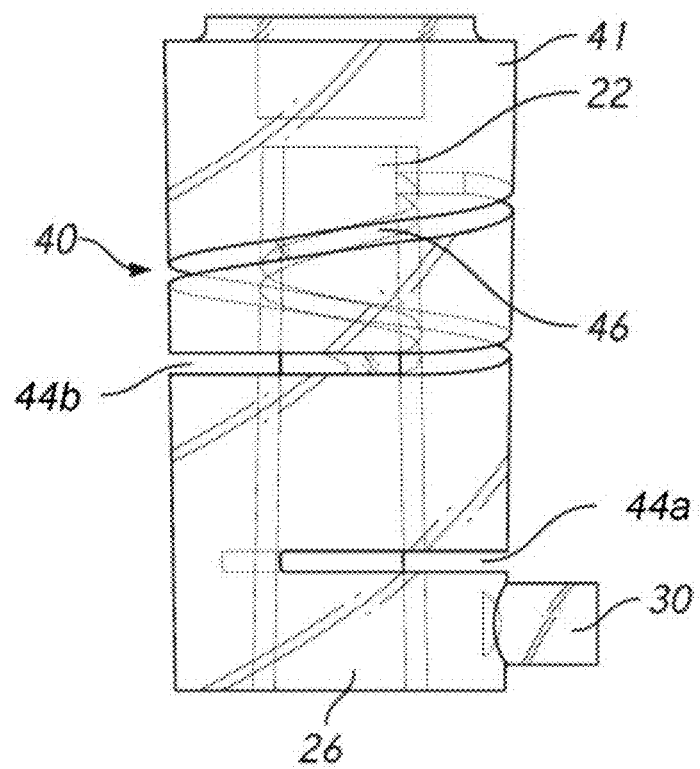
FIGS. 5-6 illustrate another example embodiment of a mixing chamber and a measuring chamber in a coaxial chamber arrangement.

FIG. 5 illustrates an example embodiment of a measurement apparatus 40. The measurement apparatus 40 may comprise a mixing chamber 41 and a measuring chamber 22. The mixing chamber 41 may comprise one or more baffles 44a, 44b. In some embodiments, the mixing chamber 41 may comprise a vane 46. In some embodiments, the mixing chamber 41 may comprise the one or more baffles 44a, 44b combined with the vane 46. Other combinations may also be possible.

As illustrated, the measurement apparatus 40 comprises two baffles 44a, 44b, but a different number of baffles may be used, such as but not limited to one, three, or four baffles. The baffle 44a may be located at or near the air inlet 30 to encourage mixing of the air and the oxygen near the entry of the air and/or the oxygen. The baffle 44b may be located further downstream from the baffle 44a. The vane 46 may be a continuation of the baffle 44b or may be located further downstream from the baffle 44b. The spacing between each of the baffles 44a, 44b and the spacing between the baffle 44b and the vane 46 may be affected by the geometry of the mixing chamber 41. In some embodiments, the spacing between the baffle 44b and the vane 46 can be similar to the spacing between each of the baffles 44a, 44b. It is to be understood that different variations of spacing between these features may exist. The baffles 44a, 44b may increase the path length that the gases travel as they move through the mixing chamber 41. The baffles 44a, 44b may induce turbulence to encourage mixing between the air and the oxygen. The positioning of the baffles 44a, 44b can be configured to enable the gases to be substantially mixed in a relatively small space. The baffles 44a, 44b can be orientated perpendicular to the direction of the flow of gases. In some embodiments, the baffles 44a, 44b can be orientated non-perpendicular to the direction of the flow of gases while still inducing turbulence to improve mixing of gases.

Figure 6:
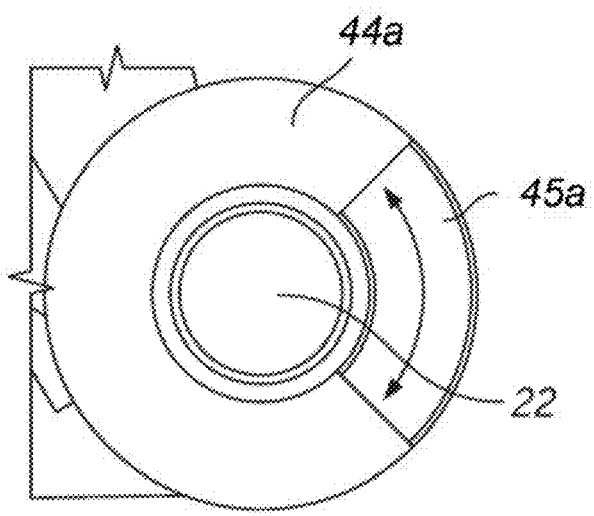

FIG. 6 illustrates that the baffles 44a, 44b extend at least partially around the measuring chamber 22, which may leave respective gaps 45a, 45b around which the baffles 44a, 44b do not extend. The baffle 44a and the gap 45a are shown in FIG. 6, but it is to be understood that the baffle 44b and the corresponding gap 45b can be configured in a similar manner. In some embodiments, the baffles 44a, 44b extend approximately 270° around the mixing chamber 41. In some embodiments, the baffles 44a, 44b extend approximately 180° around the mixing chamber 41. The baffles 44a, 44b may be configured to extend between 180° and 270° around the mixing chamber 41. The baffles 44a, 44b may also extend around the mixing chamber 41 less than 180° or greater than 270°, not including 360°. Each of the baffles 44a, 44b can extend differently around the mixing chamber 41 (e.g., the baffle 44a can extend 270° and the baffle 44b can extend 250° around the mixing chamber 41). The gaps 45a, 45b encourage the gases to spiral around the mixing chamber 41 and are located such that the gases are encouraged to mix along a greater portion of the flow path around the mixing chamber 41. The gaps 45a, 45b can be offset from one another (e.g., the gaps 45a, 45b can be not axially or longitudinally aligned with one another). The baffles 44a, 44b may comprise rounded corners to reduce flow separation and to reduce acoustic noise. In some embodiments, the baffles 44a, 44b may comprise squared corners.

The vane 46 can be configured to cause the turbulent, unsteady gases to become more laminar, enabling the gases to be substantially more stable, with fewer fluctuations, by the time they reach the measuring chamber 22. The vane 46 may also reduce pressure-induced acoustic noise in the gases delivery system 1 by reducing the turbulence of the gases. Due at least in part to the positioning of the baffles 44a, 44b, the vane 46 may increase the stability of the gases and may cause the gases to be more laminar, even at relatively high flow rates.

The measuring chamber 22 may be the inner chamber of a coaxial arrangement. Gases move from the mixing chamber 21, 41 into the measuring chamber 22. The measuring chamber 22 may comprise ultrasonic transducers, transceivers, or sensors 26 at each end, as shown in FIGS. 2, 3, and 5. In some cases, the ultrasonic sensors 26 may comprise a pair of sensors or multiple pairs of sensors. The distance between each of the ultrasonic sensors 26 may enable greater measurement resolution as compared to small changes in gases concentration. An increased distance between each of the ultrasonic sensors 26 may allow for a longer time period for acoustic signals between each of the ultrasonic sensors 26 due to the speed of sound relating to the time of flight. The distance may also decrease the sensitivity of the measurement apparatus 40 with regards to the precision of time measurements, where precision is limited by discretization error.

Ultrasonic Sensing

Each of the ultrasonic sensors 26 alternately transmits and receives pressure waves along the gases flow path. In a preferred embodiment, a first one of the ultrasonic sensors 26, configured as a transmitter, transmits a pulse series in a downstream direction along the gases flow path. A second one of the ultrasonic sensors 26, configured as a receiver, detects the transmitted pulses after a first period of time. When the transmission of the pulse series from the first one of the ultrasonic sensors 26 is complete, the configuration of the ultrasonic sensors 26 is reversed: the second one of the ultrasonic sensors 26 transmits a series of pulses in an upstream direction along the gases flow path, and the first one of the ultrasonic sensors 26 detects the transmitted pulses after a second period of time. A downstream direction is defined as a direction with or following the direction of the flow of gases along the gases flow path. An upstream direction is defined as a direction against or opposite the direction of the flow of gases (and thus opposite the downstream direction) along the gases flow path. The first and second time periods may or may not be of the same length; when they differ, generally the first time period (for the downstream transmission) will be shorter than the second time period (for the upstream transmission). Transmission and detection of pulses along the gases flow path in both directions may reduce the susceptibility of the measurement apparatus 20, 40 to system variations. In some embodiments, it is feasible to transmit only in a single direction.

Sensing along the gases flow path may allow any or all of the following gases properties or characteristics to be measured: velocity, flow rate, and/or oxygen concentration. Sensing along the gases flow path may enable these gases properties to be determined without the need for additional sensors. For redundancy and/or improvement of accuracy purposes, additional sensors, such as but not limited to temperature or humidity sensors, may be incorporated within the gases delivery system 1 without departing from the scope of the disclosed systems and methods. Sensing along the gases flow path enables the sensing to occur within a closed system. It may be advantageous for the gases delivery system 1 to be a closed system to improve the capability of the gases delivery system 1 to contain oxygen (e.g., to reduce the likelihood of oxygen leaks) and to prolong the life of plastic components in the gases delivery system 1.

The time an ultrasonic pulse takes to travel from one end of the measuring chamber 22 to the other, herein referred to as the time of flight, as well as the length and geometry of the measuring chamber 22, can be used to determine the velocity of the gases and the gases concentration based on the speed of sound. Changes in gases concentration may predictably affect the time of flight of ultrasonic signals in each direction along the gases flow path. Temperature sensors may be included in the gases delivery system 1 to enable detection of any temperature changes that may also affect changes to calculations of the speed of sound in the gases mixture.

It is to be understood that various frequencies may be used for the ultrasonic sensing and, thus, the scope of the disclosed systems and methods is not to be limited to a specific value. For purposes of an example only, in some embodiments, a frequency of approximately 25 kHz is used.

Ultrasonic sensing can provide faster responses and redundancy to the measurement apparatus 20, 40. Measurements in the measurement apparatus 20, 40 and information regarding the flow rate of the gases can be generated quickly relative to other sensing systems. Redundancy may be provided in the form of an in-built verification of measured gases properties. If an unlikely gases flow rate has been detected, this may imply that the oxygen concentration detected is incorrect. Similarly, if an unlikely oxygen concentration is detected, this may indicate that the gases flow rate is incorrect. Such redundancy may help to improve safety factors at the lower and higher extremes for flow rate. The gases that enter the measuring chamber 22 may be substantially mixed, which may reduce inconsistencies in measurements that may occur from unmixed gases.

A pulse can be defined as a peak of a single cycle associated with the driving frequency of a transducer. A pulse series may use a plurality of cycles and may detect a chosen amount of peaks. A pulse series may be defined by the period of time for which a transducer transmits the desired excitation frequency, such that a desired number of peaks may be transmitted. The number of transmitted cycles, the dispersion characteristics of the ultrasonic transducers 26 and the physical design of the measurement apparatus 20, 40 may be controlled to reduce or minimize multi-path interference in the measurement apparatus 20, 40. The time interval between transmission sequences may be configured to be shorter than the time of flight and to not cause significant interference. A single pulse may be less sensitive to the effect of multi-path interference due at least in part to the dispersion characteristics of the ultrasonic transducers 26 and the effects of the physical design of the measurement apparatus 20, 40 on the received signal.

A pulse series may be used advantageously to transmit a measurement signal that may be higher in amplitude and less sensitive to electronic noise than a single pulse. Use of the pulse series may also enable the ultrasonic sensors 26 to be excited at the driving frequency and may help to ensure that the acoustic period of the driving frequency is known, thereby removing or reducing issues that may be caused by a resonant response, such as phase delay. The driving frequency may not necessarily equal the natural frequency of the ultrasonic sensors 26, which is dependent on temperature, gases concentration, and sensor construction. The time period between when each peak may be determined from the phase shift between the transmitted signal, the received signal, and the measured temperature of the gases mixture. Peak discrimination may be easier at lower frequencies due to larger time intervals between pulses. The pulse series may yield a large sample of readings which can be processed using averaging techniques to improve accuracy.

Calculations of the speed of sound in the mixed gases can be affected by temperature and/or humidity. To improve the accuracy of calculations of the speed of sound, temperature and/or humidity corrections can be made. For example, based on properties of an ideal gas, the speed of sound is proportional to the square root of temperature. Temperature can be measured in the gases delivery system 1 for use as a correction factor. For example, temperature sensors 29 may be located at the input of the measuring chamber 22 and, in some embodiments, at the output of the measurement apparatus 20, 40 as the gases enter the humidification chamber 6 via the blower conduit 12. In some embodiments, measurement methods disclosed herein can be performed without the use of temperature corrections. In some embodiments, systems and methods disclosed herein can maintain the measuring chamber 22 at or near a targeted temperature, thus allowing calculations of the speed of sound to be performed without the use of temperature corrections.

As another example, changes in humidity may cause changes in the speed of sound of the gases. Thus, it may be desirable to measure humidity in the gases mixture to improve accuracy. These measurements can be used in calculations of the speed of sound in the gas as correction factors. To measure humidity, for example, a humidity sensor 27 may be positioned at the intake manifold of the blower assembly 2 to measure the humidity of the air entering the gases delivery system 1. In some embodiments, the humidity sensor 27 may be positioned at the outlet of the measurement apparatus 20, 40. In some embodiments, a humidity sensor can be placed both at the intake manifold of the blower assembly 2 and at the outlet of the measurement apparatus 20, 40. Use of two humidity sensors may provide the additional advantage of helping to determine the presence of a leak.

Pressure sensors 31 may be located at the oxygen inlet 32 and at the air inlet 30 of the measurement apparatus 20, 40. As a result, the static or dynamic pressure of each of the input gases can be measured as they enter the measurement apparatus 20, 40. In some embodiments, the static or dynamic pressure of the air inlet 30 can be approximated by blower speed. This may give an approximation of the ratio of the input gases composition, or the relative fraction of input gases to one another. An additional pressure sensor 31 may be located at the output of the measurement apparatus 20, 40 as the gases enter the humidification chamber 6. The measurement of pressure may provide a secondary gases concentration and a flow rate measurement system, which may be more independent of, or less sensitive to, effects of mixing, carbon dioxide, water vapour, temperature, or altitude changes. The temperature 29, humidity 29, and pressure 31 sensors may provide measurement data to improve the accuracy in the measurement of oxygen concentration. This can be achieved through direct calculations or via a lookup table.

Acoustic meta-materials may be chosen to control, manipulate, and/or direct pressure waves to reduce dispersion that may lead to interference. Such materials may be used in conjunction with, or instead of, relying on the positioning of the ultrasonic sensors 26 with respect to an appropriate aperture diameter for a measurement section that is designed according to the chosen driving frequency.

In some embodiments, the measurement apparatus 20, 40 may be used with a humidification system that is not limited to a gases source comprising a blower but instead may be attached to a ventilator, insufflator, or other gases source. In some embodiments, the measurement apparatus 20, 40 may not be a part of the blower assembly 2 but may be a separate component of the gases delivery system 1 that is located between a gases source and a humidification system.

Measurement Methods

The measurement apparatus 20, 40 can be configured to provide electrical signals to a control system that are indicative of characteristics or properties of the gases in the gases delivery system 1. The control system can receive electrical signals, determine gases properties or characteristics (e.g., gases concentration, mixing ratios, flow rate, velocity, temperature, or humidity), and control devices or components of the gases delivery system 1 at least in part in response to the electrical signals.

Figure 7:
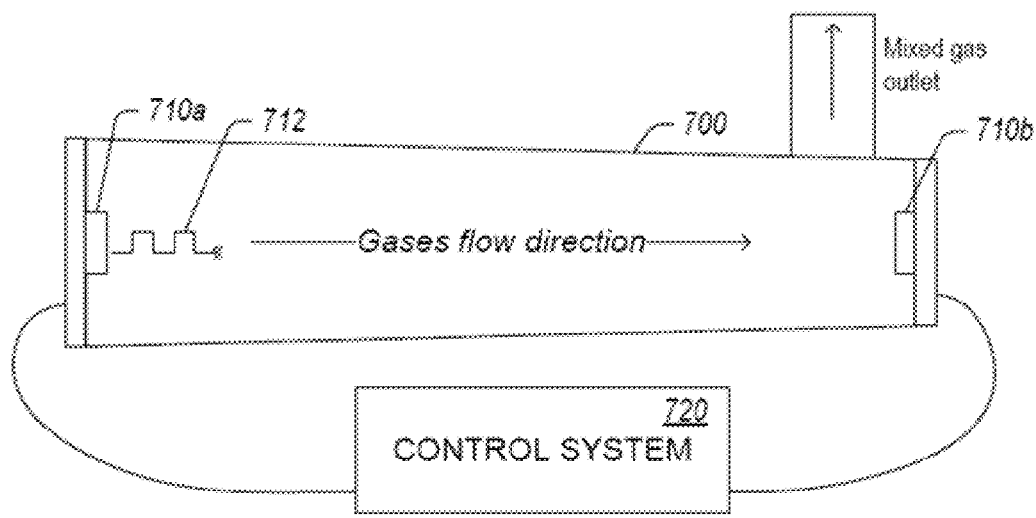
FIG. 7 illustrates an example embodiment of a measuring chamber with ultrasonic sensors at the ends of the chamber.

FIG. 7 illustrates a schematic of a measuring chamber 700 with at least two ultrasonic sensors 710a, 710b configured to measure at least one gases characteristic, where the ultrasonic sensors 710a, 710b are configured to transmit and receive pressure waves or pulses along the gases flow path. The ultrasonic sensors 710a, 710b can be configured to measure, for example and without limitation, gases concentration, flow rate, velocity, or the like. Each ultrasonic sensor 710a, 710b can be configured to transmit and receive pressure waves or pulses 712. For example, in a first measurement phase the ultrasonic sensor 710a can be configured to act as a transmitter to transmit the pulse or pulse train 712 in a downstream direction (with or following the flow of gases along the gases flow path). In this first measurement phase, the ultrasonic sensor 710b can be configured to act as a receiver to generate an electrical signal in response to the received pulses 712. In a second measurement phase, the roles of the ultrasonic sensors can be reversed—the ultrasonic sensor 710b can be switched to act as a transmitter and ultrasonic sensor 710a can be switched to act as a receiver. In this second measurement phase, the pressure waves or pulses 712 are transmitted in an upstream direction (against or opposite the flow of gases, and thus opposite the downstream direction, along the gases flow path).

The ultrasonic sensors 710a, 710b can be operably coupled to a control system 720. The control system 720 can comprise a controller, data storage, communication buses, and the like to communicate with the sensors 710a, 710b, determine gases characteristics based at least in part on signals received from the ultrasonic sensors 710a, 710b, control components of the gases delivery system 1 in response to the determined characteristics, and the like. For example, the control system 720 can be configured to determine gases characteristics by comparing the time of flight (arrival time) of the pulses 712 in each direction (from each measurement phase). The control system 720 can determine the flow rate of the gases, for example, based at least in part on the differences in time of flight. The control system 720 can control a blower, a valve, or other similar component of the gases delivery system 1 in response to the determined characteristics.

In some embodiments, the ultrasonic sensors 710a, 710b are configured to transmit and receive the pulses 712 at a frequency that is at or near a natural operating frequency of the ultrasonic sensors 710a, 710b. The ultrasonic sensors 710a, 710b can be configured to have the same natural operating frequency. This can advantageously reduce distortion from noise. In certain implementations, the natural frequency of the ultrasonic sensors 710a, 710b is about 25 kHz. In certain implementations, the ultrasonic sensors 710a, 710b can transmit and/or receive the pulses 712 about every 10 ms. The pulse train or pulses 712 can be a square wave, a sawtooth pattern, a sine wave, or some other shape of pulse. The control system 720 can be configured to identify or detect the frequency of the pulses 712 and/or the time of flight of the pulses 712. In certain implementations, the control system 720 can be configured to identify rising or falling edges, maxima or minima, and/or zero crossing points, etc., of the pulses 712. In certain implementations, sampling is done in each direction so that about 40 samples are acquired (e.g., 40 samples of rising edges and 40 samples of falling edges). In certain implementations, the sampling rate is set at about 50 Hz. In some embodiments, signals are not filtered.

Figure 8A:
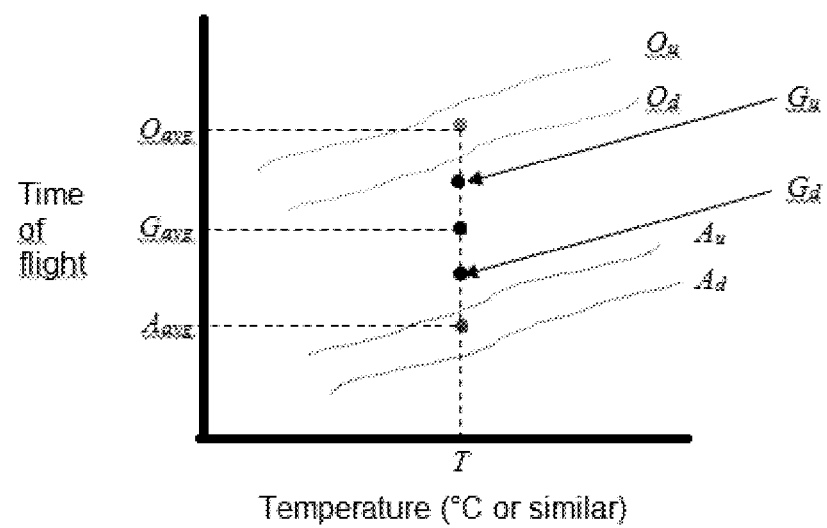
FIGS. 8A-8C illustrate example plots of measurements acquired with ultrasonic sensors to demonstrate how the control system determines gases characteristics.

With a fixed distance between the ultrasonic sensors 710a, 710b, the signal time of flight between the ultrasonic sensors 710a, 710b is affected by various characteristics or properties of the gases (e.g., oxygen levels, humidity, and temperature). At a particular temperature, the signal time of flight is expected to fall within a time range bound by the time of flight for air and for a pure oxygen environment. These time of flight boundaries are affected by factors such as gas flow, physical design of the measurement apparatus 20, 40, and assembly variations and may also be different in the downstream and upstream directions. This is illustrated in FIG. 8A, which shows a plot of a binary gas calibration curve based on example measurements of a binary gas mixture of oxygen and air using a particular embodiment of the measuring chamber 700. In FIG. 8A, the measured time of flight of pulses for an unknown mixture of gases in the downstream and upstream directions, $G_d$ and $G_u$ respectively, are plotted against a measured temperature, as is an average time of flight for both directions $G_{avg}$. Also shown in FIG. 8A are time of flight measurements at several temperatures for oxygen in the downstream and upstream directions, $O_d$ and $O_u$ respectively, and their average at the measured temperature, $O_{avg}$; and time of flight measurements at several temperatures for air in the downstream and upstream directions, $A_d$ and $A_u$ respectively, and their average at the measured temperature, $A_{avg}$. The averages for air and oxygen represent boundaries of potential time of flight measurements within the gases delivery system 1.

Figure 8B:
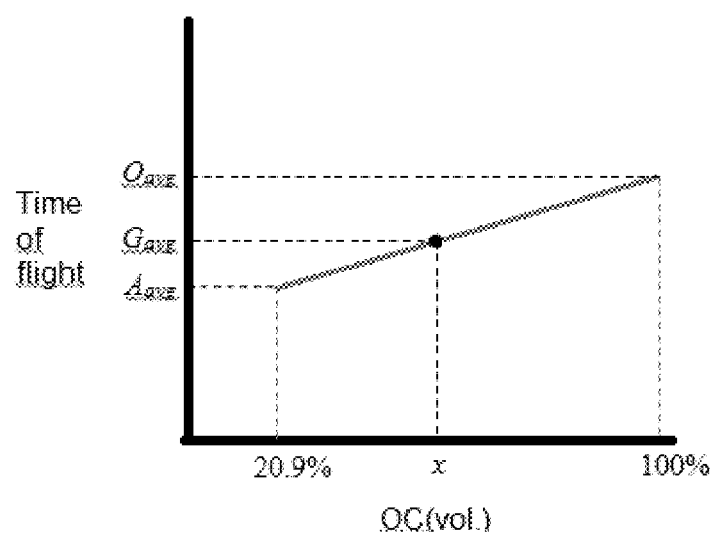

To determine an oxygen concentration of a binary gases mixture of oxygen and air, the control system 720 can be configured to identify peaks in pulse trains received by the ultrasonic sensors 710a, 710b and calculate an average time of flight in each direction based on the number of peaks received and the times of each received peak. At a particular temperature, the oxygen concentration can be calculated as a volume percentage:

$$OC(vol.) = \frac{(100 - 20.9)(G_{avg} - A_{avg})}{(O_{avg} - A_{avg})} + 20.9$$

where $$G_{avg} = \frac{(G_d + G_u)}{2}$$
$$A_{avg} = \frac{(A_d + A_u)}{2}$$
$$O_{avg} = \frac{(O_d + O_u)}{2}$$

where $G_d$ represents the downstream average time of flight for the binary gases mixture, $G_u$ represents the upstream average time of flight for the binary gases mixture, and $G_{avg}$ represents the average of $G_d$ and $G_u$; $A_d$, $A_u$, and $A_{avg}$ represent the equivalent averages for air (which is 20.9% oxygen); and $O_d$, $O_u$, and $O_{avg}$ represent the equivalent averages for 100% oxygen. In the graph in FIG. 8B, a linear relationship between the average time of flight $O_{avg}$ in 100% oxygen and the average time of flight $A_{avg}$ in an environment where there is 20.9% oxygen (e.g., air) is used to calculate the gases concentration x (e.g., the fraction of oxygen in the binary gases mixture). The line in FIG. 8B is based on the data in FIG. 8A for a given temperature (e.g., the measured temperature).

Figure 8C:
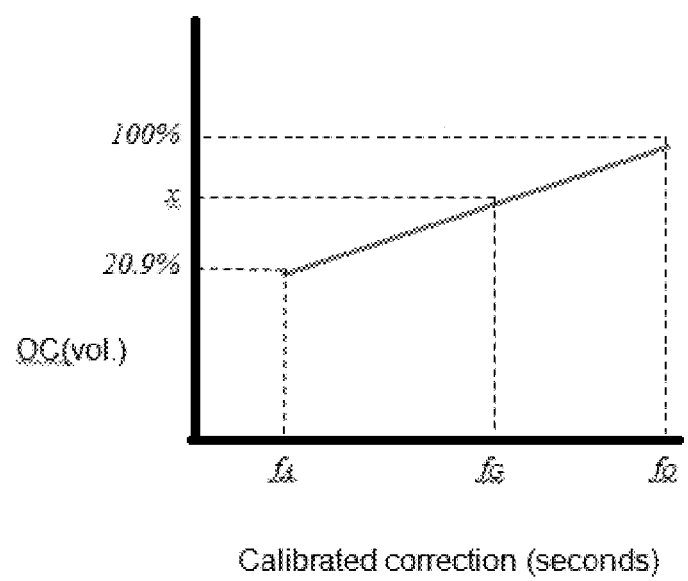

To determine the flow rate of a gases mixture comprising a particular oxygen concentration, the difference between the measured time of flight in each direction is adjusted by an offset referred to as a calibrated correction. The calibrated correction compensates at least in part for asymmetry in the measuring chamber 700. For example, even when the flow rate of gases is zero or near zero, there may be a difference in the time of flight for pulses moving in the downstream and upstream directions. As illustrated in FIG. 8C, the calibrated correction $f_G$ can be determined from a time of flight in each direction for the gases mixture based on the concentration x previously determined (e.g., as shown in FIG. 8B). As an example, the flow rate of a mixture of gas and air can be calculated, in liters per minute, as:

$$F(lpm) = k \times [(G_u - G_d) - f_G]$$

where $$f_G = f_A + \frac{(f_O - f_A)(x - 20.9)}{(100 - 20.9)}$$

where k is a constant representing the influence of the cross sectional area of the measuring chamber 700 and the distance between the ultrasonic sensors 710a, 710b, $f_A$ is a calibrated correction for air, and $f_O$ is a calibrated correction for oxygen. The calibrated correction $f_G$ is a linear interpolation between $f_A$ and $f_O$ based on gas concentration.

Unless the context clearly requires otherwise, throughout the description and the claims, the words "comprise," "comprising," "having," "including," and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The apparatus and system of the present disclosure may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the embodiments described herein will be apparent to those skilled in the art. Such changes and modifications may be made without departing from the spirit and scope of the present disclosure and without diminishing its attendant advantages. For instance, various components may be repositioned as desired or various steps in a method may be performed in differing orders. It is therefore intended that such changes and modifications be included within the scope of the present disclosure. Moreover, not all of the features, aspects and advantages are necessarily required to practice the disclosed embodiments. Accordingly, the scope of claimed embodiments is intended to be defined only by the claims that follow and not by any individual embodiment in the present disclosure.

What is claimed is:

1. A gases measurement apparatus comprising:
    a gases measuring chamber comprising a gases flow path from a first end of the gases measuring chamber to a second end of the gases measuring chamber, wherein a downstream direction is defined along the gases flow path from the first end to the second end and an upstream direction is defined along the gases flow path from the second end to the first end;
    an upstream gases flow path configured to connect a gases source to the gases measuring chamber, the upstream gases flow path comprising a gases mixing chamber coaxial with the gases measuring chamber, and further comprising a gases flow guide configured to improve laminar flow of the gases prior to entering the gases flow path of the gases measuring chamber, the gases flow guide located downstream of the gases source;
    a controller;
    the gases measuring chamber further comprising:
        a first ultrasonic sensor positioned at the first end of the gases measuring chamber, the first ultrasonic sensor configured to transmit a downstream acoustic pulse train in a first measurement phase, to detect an upstream acoustic pulse train in a second measurement phase, and to send a signal to the controller;
        a second ultrasonic sensor positioned at the second end of the gases measuring chamber, the second ultrasonic sensor configured to transmit the upstream acoustic pulse train in the second measurement phase, to detect the downstream acoustic pulse train in the first measurement phase, and to send a signal to the controller;
        a first temperature sensor at an inlet of the gases measuring chamber, the first temperature sensor configured to measure temperature of the gases flowing in the gases flow path at the inlet;
        a second temperature sensor at an outlet of the gases measuring chamber, the second temperature sensor configured to measure temperature of the gases flowing in the gases flow path at the outlet; and
        at least one pressure sensor configured to measure a pressure of the gases flowing in the gases flow path; and
    wherein the controller is configured to determine a characteristic of the gases based at least in part on the signal received from the first ultrasonic sensor, the signal received from the second ultrasonic sensor, and signals received from the first and second temperature sensors.

2. The apparatus of claim 1, wherein the gases comprise gases from two sources of gases.

3. The apparatus of claim 2, wherein the two sources of gases comprise a concentrated source of oxygen and room air.

4. The apparatus of claim 1, wherein the downstream acoustic pulse train or the upstream acoustic pulse train comprises a plurality of acoustic pulses.

5. The apparatus of claim 1, wherein the downstream acoustic pulse train or the upstream acoustic pulse train comprises a single acoustic pulse.

6. The apparatus of claim 1, wherein the characteristic of the gases comprises at least one of gases concentration, flow rate, or velocity.

7. The apparatus of claim 1, wherein the first and second ultrasonic sensors are configured to be excited at a natural resonant frequency.

8. The apparatus of claim 1, wherein the controller is configured to determine a downstream time of flight for the downstream acoustic pulse train, the controller is configured to determine an upstream time of flight for the upstream acoustic pulse train, and the controller is configured to determine the characteristic of the gases based at least in part on the downstream time of flight and the upstream time of flight.

9. The apparatus of claim 1, further comprising heat transfer features that increase heat transfer from the gases flowing through the measurement apparatus to a housing of the measurement apparatus and reduce heat transfer from the gases to an environment.

10. The apparatus of claim 9, wherein the heat transfer features are tracks formed on a surface of a printed circuit board or a moulded component, or a conductive path assembled into the measurement apparatus.

11. The apparatus of claim 1, wherein the gases measuring chamber is a part of a blower assembly of a gases delivery apparatus, the blower assembly comprising a blower, wherein the blower is the gases source.

12. The apparatus of claim 1, wherein the gases flow guide comprises a vane.

13. The apparatus of claim 1, further comprising a first humidity sensor located upstream of the gases source.

14. The apparatus of claim 13, wherein the gases measuring chamber further comprises a second humidity sensor configured to measure humidity of gases flowing in the gases flow path.

15. The apparatus of claim 14, wherein the controller is further configured to determine the characteristic of the gases based at least in part on signals received from the first and second humidity sensors.

16. The apparatus of claim 1, wherein the inlet of the gases measuring chamber comprises an oxygen inlet and an air inlet, the at least one pressure sensor comprising a first pressure sensor at the oxygen inlet and a second pressure sensor at the air inlet.

17. The apparatus of claim 16, wherein the at least one pressure sensor further comprises a third pressure sensor at the outlet.

18. The apparatus of claim 17, wherein the controller is further configured to determine the characteristic of the gases based at least in part on signals received from the first, second, and third pressure sensors.

19. A method for determining a characteristic of gases flowing through an apparatus along a gases flow path from a first end of the apparatus to a second end of the apparatus, the apparatus comprising a first ultrasonic sensor positioned at the first end and a second ultrasonic sensor positioned at the second end, a downstream direction defined along the gases flow path from the first end to the second end and an upstream direction defined along the gases flow path from the second end to the first end, the method comprising:
- transmitting a downstream acoustic pulse train from the first ultrasonic sensor and detecting the downstream acoustic pulse train at the second ultrasonic sensor;
- determining a downstream time of flight based at least in part on the downstream acoustic pulse train;
- transmitting an upstream acoustic pulse train from the second ultrasonic sensor and detecting the upstream acoustic pulse train at the first ultrasonic sensor;
- determining an upstream time of flight based at least in part on the upstream acoustic pulse train;
- determining a temperature of the gases flowing along the gases flow path at an inlet of the apparatus using a first temperature sensor;
- determining a temperature of the gases flowing along the gases flow path at an outlet of the apparatus using a second temperature sensor;
- determining the characteristic of the gases based at least in part on the downstream time of flight, the upstream time of flight, and the temperature of gases flowing along the gases flow path at the inlet and outlet of the apparatus; and
- determining a pressure of the gases flowing in the flow path using a pressure sensor,
- wherein the gases are configured to flow from a portion of the gases flow path upstream of the apparatus, the portion of the gases flow path comprising a gases flow guide configured to improve laminar flow of the gases prior to entering the apparatus, the gases flow guide located downstream of a gases source,
- wherein the apparatus comprises a single gases measuring chamber defined by a housing of the apparatus, wherein the first and second ultrasonic sensors, the first and second temperature sensors, and the pressure sensor are located at the single gases measuring chamber, and wherein the single gases measuring chamber is coaxial with a gases mixing chamber.

20. A gases delivery apparatus comprising:
a gases mixing chamber configured to receive gases from a gases source, the gases mixing chamber comprising a gases flow path from a first end of the gases mixing chamber to a second end of the gases mixing chamber and at least one mixing element situated within the gases flow path;
a humidification system; and
a gases measurement apparatus comprising:
- a gases measuring chamber configured to receive the gases from the gases mixing chamber, wherein the gases measuring chamber and the gases mixing chamber are coaxial, the gases measuring chamber comprising a gases flow path from a first end of the gases measuring chamber to a second end of the gases measuring chamber, wherein a downstream direction is defined along the gases flow path from the first end to the second end and an upstream direction is defined along the gases flow path from the second end to the first end;
- a controller; and
- the gases measuring chamber further comprising:
  - a first ultrasonic sensor positioned at the first end of the gases measuring chamber, the first ultrasonic sensor configured to transmit a downstream acoustic pulse train in a first measurement phase, to detect an upstream acoustic pulse train in a second measurement phase, and to send a signal to the controller;
  - a second ultrasonic sensor positioned at the second end of the gases measuring chamber, the second ultrasonic sensor configured to transmit the upstream acoustic pulse train in the second measurement phase, to detect the downstream acoustic pulse train in the first measurement phase, and to send a signal to the controller;
  - a first temperature sensor at an inlet of the gases measuring chamber, the first temperature sensor configured to measure temperature of the gases flowing in the gases flow path at the inlet;
  - a second temperature sensor at an outlet of the gases measuring chamber, the second temperature sensor configured to measure temperature of the gases flowing in the gases flow path at the outlet; and
  - at least one pressure sensor configured to measure a pressure of the gases flowing in the gases flow path;
wherein the controller is configured to determine a characteristic of the gases based at least in part on a signal received from the first ultrasonic sensor, a signal received from the second ultrasonic sensor, a signal from the first temperature sensor, and a signal from the second temperature sensor,
wherein the at least one mixing element is configured to mix gases in the gases flow path of the gases mixing chamber and to improve laminar flow of the gases before the gases enter the gases flow path of the gases measuring chamber, the at least one mixing element located downstream of the gases source.

21. The apparatus of claim 20, wherein the gases measurement apparatus is a separate component that is selectively removable from the gases delivery apparatus and is configured to be located between the gases source and the humidification system.

22. The apparatus of claim 20, further comprising a blower assembly that includes a blower, wherein the blower is the gases source and the gases measurement apparatus is a part of the blower assembly.

23. The apparatus of claim 22, further comprising a humidity sensor is at an intake of the blower.

24. The apparatus of claim 20, further comprising a valve to regulate the contribution of at least one of the gases to the gases mixture.

25. The apparatus of claim 20, wherein the controller is adapted to control a blower or a valve in response to the determined characteristic.

* * * * *